United States Patent
Østensen et al.

(10) Patent No.: US 6,595,925 B1
(45) Date of Patent: Jul. 22, 2003

(54) IN OR RELATING TO CONTRAST AGENTS

(75) Inventors: Jonny Østensen, Oslo (NO); Morten Eriksen, Oslo (NO); Audun Tornes, Oslo (NO); Sigmund Frigstad, Trondheim (NO)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/503,165

(22) Filed: Feb. 14, 2000

Related U.S. Application Data

(63) Continuation of application No. PCT/GB98/02481, filed on Aug. 19, 1998.

(30) Foreign Application Priority Data

Aug. 19, 1997 (GB) .............................................. 9717588

(51) Int. Cl.⁷ ................................................. A61B 8/14
(52) U.S. Cl. ..................................... 600/458; 424/9.52
(58) Field of Search ................................. 600/443, 458; 424/9.51, 9.52

(56) References Cited

U.S. PATENT DOCUMENTS

| | | | |
|---|---|---|---|
| 6,017,310 A | * | 1/2000 | Johnson et al. ............. 600/458 |
| 6,280,704 B1 | * | 8/2001 | Schutt et al. .............. 424/9.51 |

FOREIGN PATENT DOCUMENTS

| | | |
|---|---|---|
| EP | 0 324 938 A | 7/1989 |
| WO | WO 94 08627 A | 4/1994 |
| WO | WO 94 09829 A | 5/1994 |
| WO | WO 96 26746 A | 9/1996 |
| WO | WO 97 29783 A | 8/1997 |
| WO | WO 97 44067 A | 11/1997 |
| WO | WO 98 17324 A | 4/1998 |

OTHER PUBLICATIONS

Malcom Rowland and AL.; "Clinical Pharmacokinetics: concepts and applications", Lea and Febiger, Philadelphia, XP002087081.

Porter T.R.; "Detection of myocardial perfusion in multiple echocardiographic windows with one intravenous injection of microbubbles using transient response second harmonic imaging", Journal of the American College of Cardiology, Mar. 15, 1997, XP002087079.

Porter T.R. et al.; "Detection of regional perfusion abnormalities during adenosine stress echocardiography with intravenous perfluorocarbon–exposed sonicated dextrose albumin", American Heart Journal, 1996, XP002087080.

* cited by examiner

*Primary Examiner*—Francis J. Jaworski

(57) ABSTRACT

Ultrasound imaging using gas microbubble-containing contrast agents may be performed in the recirculating phase following admixture of the contrast agent with the blood pool, thereby prolonging the useful imaging time window compared to that conventionally obtained during the backscatter signal peak resulting from first pass of a contrast agent bolus. The length of the time window may further be increased by imaging at ultrasound frequencies of 2 MHz or less, particularly by harmonic imaging at transmit frequencies less than the resonance frequencies of the gas microbubbles.

22 Claims, No Drawings

IN OR RELATING TO CONTRAST AGENTS

This application is a continuation of pending international application number PCT/GB98/02481 filed Aug. 19, 1998 (of which the entire disclosure of the pending, prior application is hereby incorporated by reference).

This invention relates to gas-containing ultrasound contrast agents, more particularly to their use in diagnostic ultrasound imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas microbubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas microbubbles generated in vivo by intracardiac injection of physiologically acceptable substances have demonstrated the potential efficiency of such microbubbles as contrast agents in echography; such techniques are severely limited in practice, however, by the short lifetime of the free microbubbles. Substantial interest has accordingly been shown in methods of stabilising gas bubbles for echocardiography and other ultrasonic studies, for example using emulsifiers, oils, thickeners or sugars, or by entraining or encapsulating the gas or a precursor therefor in a variety of systems, e.g. as porous gas-containing microparticles or as encapsulated gas microbubbles, and in the selection of gases which may themselves exhibit enhanced stability and duration of echogenic effect.

Prior art concerning both the use of phospholipids as components of gas-containing ultrasound contrast agents and the selection of gases said to give improved persistence in vivo is reviewed in WO-A-9729783, the contents of which are incorporated herein by reference. WO-A-9729783 itself discloses contrast agents for use in diagnostic studies comprising a suspension in an injectable aqueous carrier liquid of gas microbubbles stabilised by phospholipid-containing amphiphilic material, characterised in that the amphiphilic material consists essentially of phosphblipid predominantly comprising molecules with net charges. The phospholipid molecules are preferably negatively charged, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins.

Contrast agents in which at least 70% of the phospholipid content consists of one or more phosphatidylserines, for example saturated (e.g. hydrogenated or synthetic) natural phosphatidylserine and synthetic or semi-synthetic dialkanoylphosphatidylserines such as distearoylphosphatidylserine, dipalmitoylphosphatidylserine and diarachidoylphosphatidylserine, are said to be preferred by virtue of their stability, minimal haemodynamic side effects and ease of elimination from the body.

Gases which may be present in such contrast agents include any substances (including mixtures) substantially or completely in gaseous (including vapour) form at the normal human body temperature of 37° C. Representative gases thus include air, nitrogen, oxygen, carbon dioxide, hydrogen, nitrous oxide, inert gases, sulphur fluorides, hydrocarbons and halogenated hydrocarbons, especially fluorocarbons such as perfluorocarbons, typically containing 1–5 carbon atoms. The use of fluorinated gases such as sulphur hexafluoride, perfluoroal kanes and perfluorocycloalkanes is particularly preferred.

Ultrasound contrast agents are usually administered intravenously as a single bolus dosage, leading to a rapid and pronounced but relatively short lasting rise in backscatter intensity in respect of blood-perfused tissue and organs as the bolus mixes with surrounding blood, thereby generating a relatively narrow and high intensity backscatter signal peak in a plot against time; backscatter measurements are normally made during the existence of this peak. This may, however, give rise to problems in, for example, the imaging of deeper tissues and organs, where high backscatter from overlying tissue during the peak period may cause excessive shadowing.

It is often desirable to prolong the useful time window for imaging beyond the relatively short duration of the backscatter signal peak resulting from passage of the contrast agent bolus. In the case of non-recirculating contrast agents, i.e. agents which are incapable of surviving more than one passage through the systemic circulation, for example as a result of instability or of specific or non-specific trapping in certain tissues, this may require repeated injection or continuous infusion of the contrast agent; however, such techniques may be inconvenient in practice and may require special pharmaceutical formulations. Use of increased dosages of non-recirculating contrast agents in an attempt to prolong the imaging time window may be limited by toxicity considerations and will frequently cause excessive acoustic shadowing, thereby significantly shortening the useful time window.

Stabilised gas microbubble-containing contrast agents such as those disclosed in WO-A-9729783 are capable of surviving passage through the systemic circulation. Such agents can pass through the pulmonary capillary bed and survive the systolic pressure changes encountered in the bloodstream, and so may provide measurable backscatter levels after mixture with the whole blood pool. In such cases a plot of backscatter intensity against time will exhibit a decay phase after the peak period as a result of the presence of echogenic contrast agent in recirculating blood; this is hereinafter referred to as the "recirculating phase". Hitherto, measurements of backscatter intensity during the recirculating phase have generally been disregarded, probably because of the low intensity levels involved. It has now surprisingly been found, however, that imaging during the recirculating phase may provide diagnostically useful results over a prolonged time period if a sufficient dosage of contrast agent is administered.

Thus the present invention is based on the finding that increasing the dose of a recirculating ultrasound contrast agent may lead to a substantial and disproportionately large increase in the useful imaging time window. Without wishing to be bound by theoretical considerations, it is thought that this unexpectedly prolonged time window may be the result of a change in the mechanism governing contrast duration. Thus, at low doses, contrast duration is determined solely by the bolus transit time, which is governed by the relationship between central blood volume and cardiac output. At high doses, on the other hand, contrast duration depends on clearance of the contrast agent from the blood, for example on the relationship between total blood volume and hepatic blood flow in the case of a contrast agent with predominantly hepatic clearance.

Thus according to one aspect of the invention there is provided a method of ultrasound imaging which comprises (i) administering an ultrasound contrast agent comprising a stabilised dispersion of gas microbubbles in an injectable carrier liquid to the vascular system of a subject in an amount which is physiologically tolerable and sufficient to generate contrast enhancement within blood in a recirculating phase following admixture of the agent with the blood pool; and (ii) generating an ultrasound image of at least a part of the vascular system of said subject during said recirculating phase.

In a further embodiment the invention provides use of stabilised gas microbubbles in the manufacture of a contrast agent for administration to the vascular system of a subject in a dosage unit which is physiologically tolerable and sufficient to generate contrast enhancement within blood in a recirculating phase following admixture of the agent with the blood pool.

The contrast agents may, for example, comprise amphiphile-stabilised, e.g. phospholipid-stabilised, gas, microbubbles, advantageously in which the phospholipids or other amphiphiles form monolayer membranes at the microbubble-carrier liquid interfaces; such agents may combine high efficacy and low toxicity by virtue of the flexibility and low material content of the stabilising membranes. The use of negatively charged phospholipids as described in WO-A-9729783 is preferred, the use of phosphatidylserines, e.g. to stabilise fluorinated gases such as perfluorobutane, being particularly preferred since the particularly low toxicity of such products facilitates their use at higher dosages.

Such contrast agents may, for example, be administered at up to 30, e.g. 5–15 times the dosage which might normally be employed for conventional imaging of tissue such as the myocardium during the peak concentration period. Thus in the case of harmonic imaging using contrast agents as described in WO-A-9729783, contrast agent doses such that the amount of phospholipid injected is in the range 2–10 $\mu$g/kg may be useful. The agents may, for example, be administered as a plurality of small doses in sequence, as a continuous infusion over an appropriate period of time or as a single high dose; this last method will generally be preferred for simplicity and convenience.

It will be appreciated that, for any given contrast agent, there will be an upper dosage limit above which shadowing will dominate for a dosage-dependent period of time, whereafter the useful imaging time window will begin; the length of the time window will remain constant at any dosage above this upper limit. The optimum dosage will therefore be one which gives substantial prolongation of the time window without causing shadowing in the recirculating phase.

Whereas imaging during the peak concentration period is typically constrained to an imaging time window of at most 4 minutes, sometimes less than 1 minute, imaging in the recirculating phase in accordance with the present procedure of tissue such as the myocardium may give an imaging time window in excess of 10, 15, 30 or even 45 minutes.

The useful imaging time window effectively ends when the backscatter from contrast agent in the recirculating phase falls to the tissue baseline level. It is therefore advantageous to use harmonic imaging techniques such as second harmonic imaging in the method of the invention, since these suppress tissue echo relative to contrast echo and will therefore extend the imaging time window. Thus, for example, a relative suppression of tissue echo by 10 dB will prolong the effective imaging time by about 3 halftimes, since $0.1 \approx (0.5)^3$.

It has also been found that imaging time windows, particularly for deeply located tissue sites, may be lengthened by use of lower than usual ultrasound imaging frequencies. It is well known that increased ultrasound frequency leads to enhanced image resolution but also results in higher attenuation; it is accordingly necessary to compromise in order to balance the requirements of adequate resolution and tissue penetration. Current diagnostic ultrasound imaging procedures typically employ frequencies of 2–10 MHz for transcutaneous measurements; thus, for example, frequencies of 2.5–5 MHz, e.g. 3.5 MHz, are commonly employed in adult cardiology and deep organ imaging.

Where highly echogenic gas microbubble-containing contrast agents are used, imaging of deeply located tissue sites of interest may be hindered as a result of attenuation (and therefore shadowing) by contrast agent in overlying tissue. Imaging of tissue in the region of interest will thus not be practicable until such attenuation has fallen sufficiently for backscatter from the tissue of interest to be determinable, thereby delaying onset of the time window for useful observations. This time window will then last until backscatter from the tissue of interest falls below the minimum level for useful observations.

The use of lower imaging frequencies, e.g. 2 MHz or less, may lengthen the imaging time window by reducing or even eliminating attenuation by contrast agent in overlying tissue and possibly also by such tissue itself, thereby advancing the time from which useful observations of the underlying tissue of interest may be made.

The imaging frequency may, for example, be in the range 1–2 MHz, and may advantageously be less than 1.8 MHz, preferably less than 1.6 MHz, for example about 1.5 MHz. The use of harmonic imaging techniques, for example second harmonic imaging, and analogous techniques such as pulse inversion imaging, may be particularly advantageous; in such cases the above-defined frequencies refer to the transmitted ultrasound signals.

It will be appreciated that such transmit frequencies are significantly below the resonance frequencies of most gas microbubble-containing contrast agents, these typically being of the order of 3–5 MHz. It has hitherto been a general belief that non-linear imaging techniques such as harmonic imaging require oscillation of microbubbles at their resonance frequency (see, for example, Ultrasonics 15(1), pp. 7–13 (1977)), so that deviation from the resonance frequency is generally considered to be disadvantageous. The finding that harmonic imaging at a transmit frequency below the resonance frequency of the microbubbles produces improved contrast to tissue signal ratios and thus substantially prolongs the useful imaging time window is therefore most unexpected.

Without wishing to be bound by theoretical considerations, it is believed that non-linear imaging such as second harmonic imaging does not in fact require the phenomenon of microbubble resonance. Thus, provided that a sufficient oscillation amplitude is experienced at the transmit frequency, non-linear oscillations may be the main source of harmonic components in the contrast obtained from contrast agent microbubbles, although not at the optimum level corresponding to resonance frequencies.

The use of lower transmit frequencies is advantageous in that attenuation is thereby reduced, allowing more power to penetrate and reach the region of interest and so giving more efficient harmonic conversion. Since, as noted above, shadowing is reduced by the use of lower frequencies, the maximum useful dose of contrast agent may be increased, thereby permitting further lengthening of the useful imaging time window.

This embodiment of the invention is particularly suited to perfusion imaging, for example myocardial perfusion imaging. It will be appreciated that spatial resolution, which may to some extent be compromised by the use of low imaging frequencies, may not be a critical parameter in such imaging.

By way of illustration of the lengthened imaging time windows which may be achieved using this embodiment, it has been found that harmonic imaging of a dog heart at 1.5 MHz produced useful results immediately after administration of a contrast agent comprising phosphatidylserine-stabilised perfluorobutane microbubbles.

Contrast agents useful in this embodiment of the invention include gas microbubbles encapsulated by flexible membranes such that they readily undergo oscillations under the influence of ultrasound energy. They may therefore, for example, comprise amphiphile-estabilised, e.g. phospholipid-stabilised gas microbubbles, for example as hereinbefore described. Again the use of negatively charged phospholipids such as phosphatidylserines, e.g. to stabilise fluorinated gases such as perfluorobutane, may be particularly advantageous.

Alternatively the contrast agent microbubbles may be less flexibly encapsulated, e.g. by stabilised protein shells, where the encapsulating material is capable of transiently softening and becoming more elastic under the influence of ultrasound energy, thereby permitting volume oscillation.

It may be advantageous during imaging in accordance with the method of the invention, especially in cardiac imaging, to induce pharmacological stress in the subject. As is well known, such stress may enhance the distinction between normally perfused healthy tissue, e.g. of the myocardium, and tissue regions supplied by stenotic arteries. Thus healthy tissue undergoes vasodilatation and increased blood flow, and may therefore exhibit significantly increased contrast echo. Blood flow in underperfused tissue supplied by a stenotic artery, on the other hand, is substantially unchanged as a result of the capacity for arteriolar vasodilatation already being exhausted by inherent autoregulation seeking to increase the restricted blood flow.

Such pharmacological stress is conveniently induced by administration, e.g. by injection, of a vasodilator, preferably while imaging is being performed during the recirculating phase.

Representative examples of vasodilators which may be used include adenosine, dipyridamole, nitroglycerine, isosbrbide mononitrate, prazosin, doxazosin, hydralazine, dihydralazine, sodium nitroprusside, pentoxyphylline, amelodipine, felodipine, isradipine, nifedipine, nimoidipine, verapamil, diltiazem and nitric oxide. Stress-inducing agents such as arbutamine and dobutamine, which have a secondary vasodilatation-inducing effect as a result of their metabolism-increasing effects, may similarly be used. Use of adenosine is particularly preferred since it is an endogenous substance and has a rapid but short-lived vasodilatating effect. This latter property is confirmed by the fact that it has a blood pool half-life of only a few seconds; possible discomfort to patients during vasodilatation is therefore minimised. Vasodilatation induced by adenosine will be most intense in the heart since the drug will tend to reach more distal tissues in less than pharmacologically active concentrations; it is therefore the vasidilator of choice in echocardiographic applications of this embodiment of the invention.

The following non-limitative Examples serve to illustrate the invention.

EXAMPLE 1

Cardiac Imaging in a Dog

An ultrasound contrast agent prepared as in Example 2(b) of WO-A-9729783 was injected intravenously into an anaesthetised dog as an intravenous bolus at dose levels corresponding to 1, 9 and 30 times the normal dose for imaging of the first-pass bolus effect, i.e. at doses corresponding to 0.03, 0.27 and 0.9 $\mu$l of gas per kg body weight of the dog. The myocardium was imaged with an ATL HDI-3000 scanner equipped with a P3-5 transducer, operating in harmonic mode with a transmitted frequency of 2.1 MHz and a received frequency of 4.2 MHz. One image was recorded in each end-systole, using ECG gating. The useful imaging time windows for the different doses were respectively found to be 45 seconds, 7 minutes and in excess of 45 minutes.

EXAMPLE 2

Cardiac Imaging in a Human

An ultrasound contrast agent prepared as in Example 2(b) of WO-A-9729783 is injected intravenously into a patient with a known left anterior descending coronary artery stenosis, as an intravenous bolus of 0.15 $\mu$l of gas per kg body weight of the patient. This corresponds to 5 times the normal dose for imaging of the first-pass bolus effect. The heart is imaged with a Hewlett Packard Sonos 2500 scanner operating in second harmonic mode with a transmitted frequency of 1.8 MHz, with the transducer in the parasternal short axis position. One end-systolic image is recorded every second heartbeat. After 5 minutes, still in the useful imaging time window, an infusion of adenosine is started at a rate of 140 $\mu$g/kg/minute. Some 30 seconds later, an increase in regional contrast echo intensity is seen in that part of the myocardium supplied by normal arterial branches; the area supplied by the stenotic artery does not show such an increase.

EXAMPLE 3

Imaging at Lower Frequencies

In a similar procedure to that described in Example 1, using the same brand of scanner and settings, imaging was performed using either a P3-2 transducer transmitting at 1.8 MHz or a P5-3 transducer transmitting at 2.1 MHz. The contrast agent was repeatedly injected at a dose level corresponding to 0.03 $\mu$l of gas per kg body weight of the dog. Apparent contrast enhancement of the myocardium was more intense with the P3-2 transducer, and ultrasound signal attenuation in the blood-filled left ventricle during peak bolus passage was observed to be less with this transducer. Additionaly, the duration of adequate contrast effect after the initial phase of ventricular attenuation was greater using the P3-2 transducer.

What is claimed is:

1. A method of ultrasound imaging which comprises
   (i) administering an ultrasound contrast agent comprising a stabilised dispersion of gas microbubbles in an injectable carrier liquid to the vascular system of a subject in an amount which is physiologically tolerable and which is sufficient to generate diagnostically useful contrast enhancement within blood in a recirculating phase following admixture of the agent with the blood pool for an imaging time window in excess of 10 minutes; and
   (ii) generating an ultrasound image of at least a part of the vascular system of said subject during said recirculating phase.

2. A method as claimed in claim 1 wherein the administering step comprises administering a contrast agent which comprises gas microbubbles stabilised at the gas-carrier liquid interfaces by monolayers of amphiphilic material.

3. A method as claimed in claim 2 wherein in the contrast agent administering step said amphiphilic material comprises at least one phospholipid.

4. A method as claimed in claim 3 wherein in the contrast agent administering step said amphiphilic material consists essentially of phospholipid predominantly comprising molecules which individually have an overall net charge.

5. A method as claimed in claim 4 wherein in the contrast agent administering step substantially all of the phospholipid consists of molecules which individually have an overall net negative charge.

6. A method as claimed in claim 5 wherein in said contrast agent administering step one or more phosphatidylserines constitute at least 70% of the phospholipid.

7. A method as claimed in claim 1 wherein in said contrast agent administering step the gas microbubbles comprise sulphur hexafluoride or a perfluorinated low molecular weight hydrocarbon.

8. A method as claimed in claim 7 wherein in said contrast agent administering step the perfluorinated low molecular weight hydrocarbon is perfluorobutane.

9. A method as claimed in claim 1 wherein in step ii) an imaging frequency of 2 MHz or less is transmitted.

10. A method as claimed in claim 1 wherein in step (ii) the ultrasound image is generated using a non-linear imaging technique.

11. A method as claimed in claim 10 wherein the ultrasound image is generated by second harmonic imaging.

12. A method as claimed in claim 10 wherein the contrast agent comprises gas microbubbles stabilised at the gas-carrier liquid interfaces by monolayers consisting essentially of phospholipid which predominantly comprises molecules which individually have an overall net charge, and said contrast agent is administered in a dose corresponding to 2–10 $\mu$g of phospholipid per kg body weight of the subject.

13. A method as claimed in claim 10 wherein in step (ii) the ultrasound image is generated using a transmit frequency below the mean resonance frequency of the gas microbubbles.

14. A method as claimed in claim 10 wherein in step (ii) the ultrasound image is generated using a transmit frequency of 2 MHz or less.

15. A method as claimed in claim 14 wherein the transmit frequency is about 1.5 MHz.

16. A method as claimed in claim 1 wherein pharmacological stress is induced in the subject during the ultrasound imaging.

17. A method as claimed in claim 16 wherein pharmacological stress is induced by administration of a vasodilator to the subject.

18. A method as claimed in claim 17 wherein in said pharmacological stress inducing step said vasodilator is adenosine.

19. A method as claimed in claim 17 wherein the vasodilator is injected into the subject during ultrasound imaging in the recirculating phase.

20. A method as claimed in claim 1 wherein the contrast agent is administered in an amount sufficient to generate diagnostically useful contrast enhancement within blood in the recirculating phase for an imaging time window in excess of 15 minutes.

21. A method as claimed in claim 20 wherein the contrast agent is administered in an amount sufficient to generate diagnostically useful contrast enhancement within blood in the recirculating phase for an imaging time window in excess of 30 minutes.

22. A method as claimed in claim 21 wherein the contrast agent is administered in an amount sufficient to generate diagnostically useful contrast enhancement within blood in the recirculating phase for an imaging time window in excess of 45 minutes.

* * * * *